United States Patent
Panin

(10) Patent No.: US 9,693,751 B2
(45) Date of Patent: Jul. 4, 2017

(54) PATIENT BASED DETECTOR CRYSTAL QUALITY CONTROL FOR TIME OF FLIGHT ACQUISITION

(71) Applicant: Siemens Medical Solutions USA, Inc., Malvern, PA (US)

(72) Inventor: Vladimir Y. Panin, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 161 days.

(21) Appl. No.: 14/676,876

(22) Filed: Apr. 2, 2015

(65) Prior Publication Data
US 2015/0297168 A1    Oct. 22, 2015

Related U.S. Application Data

(60) Provisional application No. 61/981,274, filed on Apr. 18, 2014.

(51) Int. Cl.
| | |
|---|---|
| *A61B 6/03* | (2006.01) |
| *A61B 6/00* | (2006.01) |
| *A61N 5/10* | (2006.01) |
| *G01T 1/29* | (2006.01) |
| *G01T 7/00* | (2006.01) |

(52) U.S. Cl.
CPC ............ *A61B 6/585* (2013.01); *A61B 6/037* (2013.01); *A61B 6/4258* (2013.01); *A61B 6/583* (2013.01); *A61N 5/1049* (2013.01); *G01T 1/2985* (2013.01); *G01T 7/005* (2013.01); *A61N 2005/1052* (2013.01); *A61N 2005/1087* (2013.01)

(58) Field of Classification Search
CPC ..................................................... A61B 6/037
See application file for complete search history.

(56) References Cited

U.S. PATENT DOCUMENTS 8,110,805 B2 *   2/2012   Panin ................... G01T 1/1648
                                                       250/362

* cited by examiner

*Primary Examiner* — Tse Chen
*Assistant Examiner* — Jason Ip

(57) ABSTRACT

Disclosed herein too is a positron emission tomography calibration system comprising a positron emission tomography scanner having a ring detector that comprises at least one bin for receiving radiation; a patient that is placed at approximately the center of the ring detector where the patient is irradiated with at least one dose of a treatment radiation beam; a crystal efficiency calibration system that performs the following: measures activity generated by the at least one defined radiation dose in the at least one bin; takes projection data of the measured activity; calculates crystal efficiency from the projection data; re-estimates the measured activity of each bin based on the calculated crystal efficiency; and calibrates the detector based on the re-estimated measured activity.

18 Claims, 6 Drawing Sheets

(A)

(B)

(C)

(D)

(E)

PATIENT BASED DETECTOR CRYSTAL QUALITY CONTROL FOR TIME OF FLIGHT ACQUISITION

RELATED APPLICATIONS

This disclosure claims the benefit of U.S. Provisional Patent Application No. 61/981,274 filed on Apr. 18, 2014, the entire contents of which are hereby incorporated by reference.

BACKGROUND

This disclosure relates to patient-based detector crystal quality control for time of flight data acquisition. In particular, this disclosure relates to patient-based detector crystal quality control for time of flight data acquisition in positron emission tomography systems.

Positron emission tomography (PET) is an imaging method that is used in nuclear medicine and radiation therapy. During PET, a positron is emitted in a body due to radioactive decay. After a short distance, the positron enters into interaction with an electron. The interaction destroys both particles. The destruction creates a pair of gamma quanta. The quanta are at an angle of 180° from one another. The gamma quanta penetrate the body to be examined and after exiting it are recorded by two opposed detectors. A positron emission tomography scanner for imaging includes a plurality of gamma radiation detectors, which surround the patient to be examined.

The relevant radioactive decay may be induced, for example, by injection or inhalation of a radioactively marked radiopharmaceutical, such as a tracer. Disease information may be determined based on the spatial distribution of the tracer.

Radioactive decay involving the formation of positrons occurs during radiation therapy from the irradiation of a body, for example, as a function of the radiation dose applied. PET systems may perform such dosage validation or monitoring of the radiation therapy and particle therapy. In particle therapy, measurements are performed in order to check whether the planned radiation dose matches the dose actually applied and/or whether the spatial distribution of an applied dose matches a desired spatial distribution.

PET systems may be used with a particle therapy system and may deviate from the conventional ring form. For example, an in-beam PET system may include only two opposed detectors. The additional opening between the two detectors, for example, may be used to position the patient, or irradiate the patient with a beam passing through this opening without the beam striking the detectors.

To enable precise dosage validation, PET systems are calibrated at certain time intervals, for example, daily. Radioactive sources may be used for calibration. The radioactive sources are disposed in a treatment chamber in which the PET system is also located. The radioactive sources generate a defined activity, which is measured by the PET system. The measurements are used to calibrate the PET system. This process may, for example, include checking an existing calibration of the PET system.

PET scanner calibration is a routine procedure that is performed daily in order to provide accurate results when a patient is subjected to a scan. In some scanners, for example, data are acquired for about 20 to 30 minutes each day using a 20 centimeter (cm) diameter uniform cylinder. By assuming a known object (e.g., the 20 cm diameter uniform cylinder) an estimation of a crystal-efficiency normalization component is conducted, since the rest of the normalization components are fixed for a given scanner type.

Normalization factors are corrections that compensate for non-uniformity of PET detector pair efficiencies. A component-based method is used to improve accuracy of the normalization factors. Most components, such as geometric and crystal interference components, can be estimated in advance for a particular scanner type. This is contrary to the crystal efficiency component, which is estimated on a regular basis. Besides producing a normalization array, the crystal efficiency values are used in daily Quality Control (QC) procedures. In this procedure, particular block crystal sensitivities are checked against average block crystal sensitivities. A significant deviation of the block from an average one will signal for replacement or monitoring of this block. Potentially, data originating from this particular block can be excluded during list mode data histogramming and reconstruction.

The use of frequent phantom scans is not ideal. Self-normalization (estimation of the normalization array from unknown object data) was suggested as an alternative, but in non-TOF (time of flight), an acceptable solution can be achieved only with the use of significant a priori knowledge. The TOF self-normalization problem was proposed in, where crystal efficiencies were estimated with the help of detector singles measurements. However, such measurements are not available on all scanners. Similar information can be extracted from random events data on Siemens scanners. However, this singles estimation is of a low count nature and is used for random variance reduction. Singles modeling is equivalent to a non-collimated single-photon emission computed tomography (SPECT) problem formulation. This requires the development of an additional reconstruction model. Finally, singles efficiencies may not correlate well with efficiencies for coincidence events.

Calibration is therefore complicated, since dedicated radioactive sources have to be set up in the treatment chamber and then removed. This process requires manual intervention, involves cost, and can suffer from errors.

SUMMARY

Disclosed herein is a method for calibrating a positron emission tomography detector of a radiation therapy device, the method comprising applying, using a radiotherapy device, at least one defined radiation dose in a living sample body to induce a defined activity in the living sample body, the at least one defined radiation dose being applied by irradiating the living sample body with a treatment radiation beam of the radiotherapy device; where the positron emission tomography detector comprises at least one bin; measuring the activity generated by the at least one defined radiation dose in the at least one bin; taking projection data of the measured activity; calculating crystal efficiency from the projection data; re-estimating the measured activity of each bin based on the calculated crystal efficiency; and calibrating the bin based on the re-estimated measured activity.

Disclosed herein too is a positron emission tomography calibration system comprising a positron emission tomography scanner having a ring detector that comprises at least one bin for receiving radiation; a patient that is placed at approximately the center of the ring detector where the patient is irradiated with at least one dose of a treatment radiation beam; a crystal efficiency calibration system that performs the following: measures activity generated by the at least one defined radiation dose in the at least one bin;

takes projection data of the measured activity; calculates crystal efficiency from the projection data; re-estimates the measured activity of each bin based on the calculated crystal efficiency; and calibrates the detector based on the re-estimated measured activity.

BRIEF DESCRIPTION OF THE FIGURES

FIGS. 6(C)-(E) show curves corresponding to estimates from phantom data, and those that correspond to estimates obtained from patient data.

DETAILED DESCRIPTION

Figure 1:
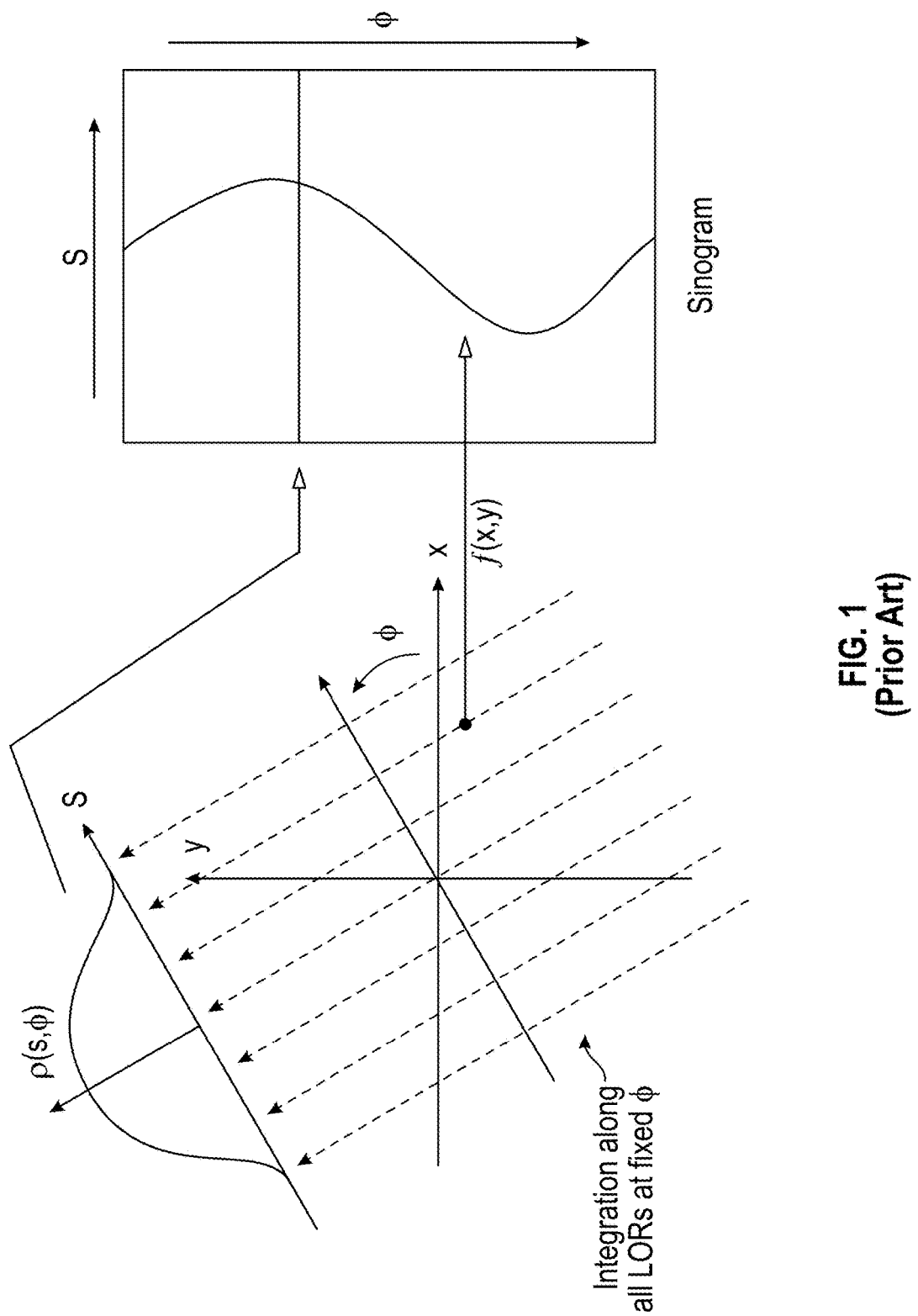
FIG. 1 is a prior art diagram illustrating an example of the relationship between positron emission data and a sinogram.

Disclosed herein is a scanner calibration method for positron emission tomography that includes simultaneous reconstruction of activity and crystal efficiencies from time of flight (TOF) data. By taking into consideration of time of flight, a simultaneous estimation can be made of the patient image as well as the normalization crystallization efficiency component. In an embodiment, for each line of response (LOR), attenuation can be estimated from time of flight (TOF) data of an unknown object. This formalism can be applied to a normalization array estimation instead of exclusively to the attenuation. The normalization array can be further constrained by crystal efficiencies which are not known. Therefore, the scanner performance can be monitored as patient scans occur, eliminating the need for the frequent calibration scans using phantoms. This method is advantageous in that it significantly simplifies scanner usage in a clinical environment.

In the method disclosed herein, a positron emission tomography device is used to apply at least one defined radiation dose in a sample body to induce a defined activity in the sample body. In an exemplary embodiment, the sample body is not a phantom but is an actual patient. The at least one defined radiation dose is applied by irradiating the sample body with a treatment radiation beam of the device. The sample body is generally the body of a living being (i.e., a patient). A visual representation of the raw data is obtained in a scan called a sinogram. Each bin (also referred to herein as a pair of detectors) of the scanner that produces the sinogram is corrected by detection efficiency. The sinogram is subjected to self-normalization, though the fixed part of self-normalization is no longer used. In this self-normalization, the time of flight data is used to calculate crystal efficiency. The activity image can be estimated from coincidence information.

In short, the scanner is calibrated by measuring the activity generated by the at least one defined radiation dose where each bin (of the detector) of the modeled sinogram is corrected by detection efficiency. Components of normalization may be obtained by matching a known object modeled sinogram with its measured sinogram if desired. If a particular bin deviates from a desired or pre-calibrated value it can be ignored (i.e., shut off manually or electronically) or replaced with a new bin that performs within the desired specification. Alternatively, the bin can be subjected to further monitoring.

PET is used to produce images for diagnosing the biochemistry or physiology of a specific organ, tumor or other metabolically active site. The measurement of tissue concentration using a positron emitting radionuclide is based on coincidence detection of the two gamma photons arising from a positron annihilation. When a positron is annihilated by an electron, two gamma photons (having energies of 511 keV) are simultaneously produced and travel in approximately opposite directions. Gamma photons produced by an annihilation event can be detected by a pair of oppositely disposed radiation detectors (bins) capable of producing a signal in response to the interaction of the gamma photons with a scintillation crystal. Annihilation events are generally identified by a time coincidence between the detection of the two gamma photons in the two oppositely disposed detectors; i.e., the gamma photon emissions are detected virtually simultaneously by each detector. When two oppositely disposed gamma photons each strike an oppositely disposed detector to produce a time coincidence event, they also identify a line(s)-of-response (LOR) along which the annihilation event has occurred. An example of a PET method and apparatus is described in U.S. Pat. No. 6,858,847, the entire contents of which are incorporated herein by reference. Using statistics collected from tens of thousands of coincidence events, a set of simultaneous equations for the total activity of each parcel of tissue along many LORs can be solved by a number of techniques, and, thus, a map of radioactivities as a function of location for parcels or bits of tissue (also called voxels) can be constructed and plotted. The resulting map shows the tissues in which the molecular tracer has become concentrated, and can be interpreted by a nuclear medicine physician or radiologist in the context of the patient's diagnosis and treatment plan.

After being sorted into parallel projections, the LOR defined by the coincidence events are used to reconstruct a three-dimensional distribution of the positron-emitting radionuclide within the patient. In two-dimensional PET, each 2D transverse section or "slice" of the radionuclide distribution is reconstructed independently of adjacent sections. In fully three-dimensional PET, the data are sorted into sets of LOR, where each set is parallel to a particular detector angle, and therefore represents a two dimensional parallel projection p(s, φ) of the three dimensional radionuclide distribution within the patient—where "s" corresponds to the distance of the LOR from the center of the detector and "φ" corresponds to the angle of the detector plane with respect to the x axis in (x, y) coordinate space (in other words, φ corresponds to a particular LOR direction).

Coincidence events are integrated or collected for each LOR and stored in a sinogram. In this format, a single fixed point in f(x, y) traces a sinusoid in the sinogram. In each sinogram, there is one row containing the LOR for a particular azimuthal angle φ; each such row corresponding to a one-dimensional parallel projection of the tracer distribution at a different coordinate along the scanner axis. This is shown conceptually in the FIG. 1.

An event is registered if both crystals detect an annihilation photon within a coincidence time window T (e.g., on the order of 4-5 nano-seconds), depending on the timing properties of the scintillator and the field of view (FOV). The FOV is defined as the volume between the detectors; and a pair of detectors is sensitive only to coincidence events occurring in the FOV. Therefore, the need for physical collimation is eliminated and sensitivity is significantly increased. Accurate corrections (for example, attenuation correction) can be made for the self-absorption of photons within the patient so that accurate measurements of tracer concentration can be made.

The number of time coincidences detected per second within a FOV of a detector is the count rate of the detector. The count rate at each of two oppositely disposed detectors, A and B, can be referred to as singles counts or $S_A$ and $S_B$, respectively. The time used for a gamma photon to travel from its point of origin to a point of detection is referred to as the time-of-flight (TOF) of the gamma photon. TOF is dependent upon the speed of light c and the distance traveled. A time coincidence or coincidence event is identified if the time difference between the arrivals of signals in a pair of oppositely disposed detectors is within the coincidence time window T. In conventional PET, the coincidence detection time window T is wide enough so that an annihilation event occurring anywhere within the object will produce annihilation gamma photons reaching their respective detectors within the coincidence window. Coincidence time windows of 4.5-12 nanoseconds are common for conventional PET, and are largely determined by the time resolution capabilities of the detectors and electronics.

Figure 2:
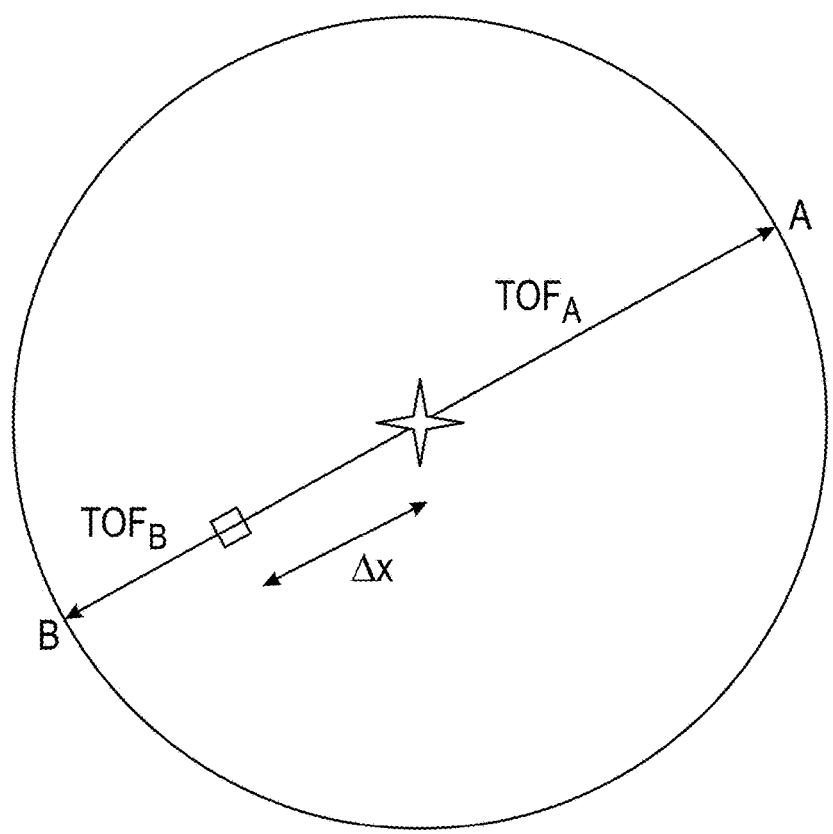
FIG. 2 is a prior art diagram illustrating the concept of time-of-flight (TOF) in positron emission tomography (PET) imaging.

As illustrated in the FIG. 2, if an annihilation event occurs at the midpoint of a LOR, the TOF of the gamma photon detected in detector A ($T_A$) is equal to the TOF of the gamma photon detected in detector B ($T_B$). If an annihilation event occurs at a distance Δx from the midpoint of the LOR, the difference between $T_A$ and $T_B$ is Δt=2Δx/c, where c is the speed of light. If d is the distance between detectors, the TOF difference Δt could take any value from −d/c to +d/c, depending on the location of the annihilation event.

Time-of-flight (TOF) positron emission tomography (PET) ("TOF-PET") is based on the measurement of the difference Δt between the detection times of the two gamma photons arising from the positron annihilation event. This measurement allows the annihilation event to be localized along the LOR with a resolution of about 75-120 millimeter (mm) full width at half maximum (FWHM), assuming a time resolution of 500-800 ps (picoseconds). Though less accurate than the spatial resolution of the scanner, this approximate localization is effective in reducing the random coincidence rate and in improving both the stability of the reconstruction and the signal-to-noise ratio (SNR), especially when imaging large objects. Thus, in TOF-PET, the "TOF" coordinate, Δt, is stored together with s and φ.

Recent theoretical advances have demonstrated that attenuation (non-TOF distribution) can be extracted from TOF emission data by using a scaling parameter for each line-of-response (LOR). However, the normalization is not separable from attenuation factors, as long as the normalization is assumed to be a non-TOF distribution. One can therefore estimate normalization directly from emission data, assuming a known attenuation distribution. Nevertheless, such similar-to-direct normalization estimations are unlikely to be useful due to significant noise in the emission data. This problem is circumvented by using a special class of algorithms, ML-ACF (Maximum Likelihood-Activity Attenuation Correction Factors). ML-ACF provides for a maximum likelihood estimation of attenuation factors and activity. The scattering event modeling takes part in the efficiencies estimation. The model equations are non-linear with respect to efficiencies at the known activities. The Maximum Likelihood Activity and Crystal Efficiencies (ML-ACE) algorithm is detailed further below.

TOF prompt data y with spatial projection (LOR) index j and TOF bin index t can be modeled by combining the modeled projection $\bar{p}$ from the emission object f, corrected for scanner efficiency by a normalization array n and for attenuation by a, and scatter estimation S, corrected for scanner efficiency as well, and mean random data $\bar{r}$:

$$\bar{y}_{jt} = a_j n_j^{-1}(\varepsilon) \sum_k C_{jt,k} f_k + n_j^{-1}(\varepsilon) S_{jt} + \bar{r}_j = \qquad (1)$$

$$a_j n_j^{-1}(\varepsilon) \bar{p}_{jt}(f) + n_j^{-1}(\varepsilon) S_{jt} + \bar{r}_j,$$

where $C_{jt,k}$ is the system matrix. The normalization data model represents the mashing and rebinning of the LORs connecting two crystals i and i' into the projection bin of index j:

$$n_j^{-1}(\varepsilon) \sum_{i,i'} \omega_{j,ii'} g_{ii'} \varepsilon_i \varepsilon_{i'}, \qquad (2)$$

where ε is the crystal efficiency and g is the geometrical component of the normalization array.

The ω is the LOR contribution factor:

$$\omega_{j,ii'} = \begin{cases} 1/2, & \text{if } ii' \text{ contribute to sinogram bin } j \\ 0, & \text{otherwise} \end{cases} \qquad (3)$$

The following objective function is to be maximized:

$$L(\varepsilon, f) = \sum_{jt} (y_{jt} \ln(\bar{y}_{jt}) - \bar{y}_{jt}). \qquad (4)$$

The optimization is performed by iterations; each is divided into two steps. This iterative scheme is denoted as the Maximum Likelihood Activity and Crystal Efficiencies (ML-ACE) algorithm. The first step is activity update with the fixed normalization (efficiencies) array. A commonly used ML(OS)-EM algorithm is used. Corresponding notations are omitted for simplicity. TOF ordered-subsets expectation-maximization (OS-EM) activity reconstruction is performed with a plurality of iterations and a plurality of subsets. In an embodiment, TOF OS-EM activity reconstruction is performed with 1 iteration and 21 subsets.

The second step is the efficiencies update by the iterative algorithm, developed for the daily calibration scan, where the activity distribution is known. This step can be presented by the series of Equations (5) below:

$$\varepsilon_i^{(N+1)} = \frac{-B_i + \sqrt{B_i^2 + 4A_i C_i}}{2A_i} \quad (5)$$

$$A_i = \sum_{jt} \sum_{i'} \omega_{j,ii'} g_{ii'} (a_j \bar{p}_{jt}(f) + S_{jt}),$$

$$B_i = \sum_{jt} \sum_{i'} \omega_{j,ii'} (a_j \bar{p}_{jt}(f) + S_{jt}) \varepsilon_{i'}^{(N)} - A_i \varepsilon_i^{(N)}$$

$$C_i = \varepsilon_i^{(N)} \sum_{jt} \frac{y_{jt}}{\bar{y}_{jt}^{(N)}(f, \varepsilon^{(N)})} \sum_{i'} \omega_{j,ii'} (a_j \bar{p}_{jt}(f) + S_{jt}) \varepsilon_{i'}^{(N)},$$

where N is the iteration number for the update of efficiencies. In actual practice, N can be any integer from 1 to 50. In an exemplary embodiment, N=4. Each step uses a simultaneous update algorithm. The two steps performed together, however, represent the sequential update algorithm.

The initial condition was efficiencies-initiated by the average block values and uniform activity distribution. A plurality of iterations may be carried out. In an exemplary embodiment, three iterations of ML-ACE were performed. This is detailed in the Example below. This effectively results in three iterations and 21 subsets of OS-EM activity reconstruction and this corresponds approximately to clinical use. Effectively, 12 iterations of efficiencies estimation may be carried out. This corresponds approximately to algorithm use in a calibration scan, where ten iterations are generally carried out.

The crystal efficiencies estimation is generalized with TOF mashing and axial rebinning. The ω, the LOR contribution factor, will be TOF dependent in this problem formulation.

The algorithm and the method described herein is exemplified in the following non-limiting example.

EXAMPLE

This example was conducted to demonstrate the use of the ML-ACE algorithm in scanner calibration. A 4 ring Siemens mCT (computed tomography) scanner was used in the example. The scanner consists of four block wide rings with 48 blocks in the ring transverse direction. Each block consists of 13×13 LSO crystals that are 4×4×20 mm each. The mCT non-TOF sinogram contains 400 radial bins, 168 azimuthal views (factor 2 non-TOF mashing), 621 axial direct and oblique planes, and span 11 non-TOF axial compression.

The gold standard efficiencies estimation was performed using data acquired from a 20 cm diameter, approximately 21 cm long, uniform cylinder. Data were acquired in the list mode format. A short duration sinogram of 900 seconds duration was produced, with 2×10$^8$ trues. The scanner underwent full setup before the example was conducted. A standard normalization array was produced. Nevertheless, a few blocks degraded at the moment of data acquisition. An original normalization array was used in the scatter estimation, though it was not fully consistent with the scanner condition at the moment of scanning. The scatter component is estimated with an assumption of smooth distribution and therefore it is relatively insensitive to possible normalization artifacts.

During histogramming of the list mode file, a fraction of counts acquired on LORs that originated in the first eight blocks was withdrawn. This artificially created hot spots in the affected block sensitivities map. The central nine (3×3) crystals maintained original sensitivities, while the rest of the crystals lost 50% of their original sensitivities. Recovery of hot spots was computed as the ratio of the central crystal in an affected block to the central crystal of a neighboring block. Recovery was averaged over all eight affected blocks. In order to understand the noise property, the standard deviation of each crystal efficiency in block (total 13×13) over all blocks, normalized by the average block efficiency value was computed. Noise was computed as the average standard deviation over all 13×13 crystals. Forty blocks (10×4) were used in the noise assessment. Recovery of hot spots versus noise in the crystal efficiencies estimation was considered as a function of the iteration number to understand the algorithm convergence properties. Note that in the case of phantom data, the object is known and data are summed over the TOF dimension. Only the iterative procedure represented by formula (5) above is used.

The method was tested for data acquired on the Siemens mCT four ring scanners. Two data sets were used to show various artifacts. The first data set consisted of seven beds of acquisition with a duration of 140 seconds per bed. Five beds corresponding to a patient torso were reconstructed with no artifacts in the crystal efficiencies. Five beds contained 1.1×10$^8$ trues. The rest of the beds corresponded to the areas of a neck, head, and arms of a patient. The corresponding reconstruction was used to display crystal efficiencies artifacts due to mis-positioned arms on the attenuation map.

The second data set consisted of seven bed acquisitions with durations of 150 seconds per bed. Five beds, corresponding to the torso region, together contained 1.3×10$^8$ trues. This data set was acquired in list mode file. In addition, a procedure was performed where hot spots were created in the first eight blocks.

The activity reconstructions were on a 2×2×2 mm grid. The reconstructed images were post-smoothed by a 6 mm Gaussian filter. Crystal efficiencies maps were reconstructed separately for each bed's data and averaged over all bed reconstructions.

The attenuation correction was based on the computed tomography (CT) image. The scatter correction was computed with the provided crystal efficiencies map in the normalization file. This file explicitly contains the crystal efficiencies map from the calibration scan. This efficiency distribution was considered to be the gold standard for a given patient data set. Note that no exact comparison of the gold standard to the ML-ACE estimation can be performed. The gold standard estimation was performed with the use of a uniform initial condition for crystal efficiencies. A different iterative algorithm was used as well. An earlier version of the Siemens reconstruction software employs a Gaussian model in the crystal efficiencies estimation.

Figure 3:
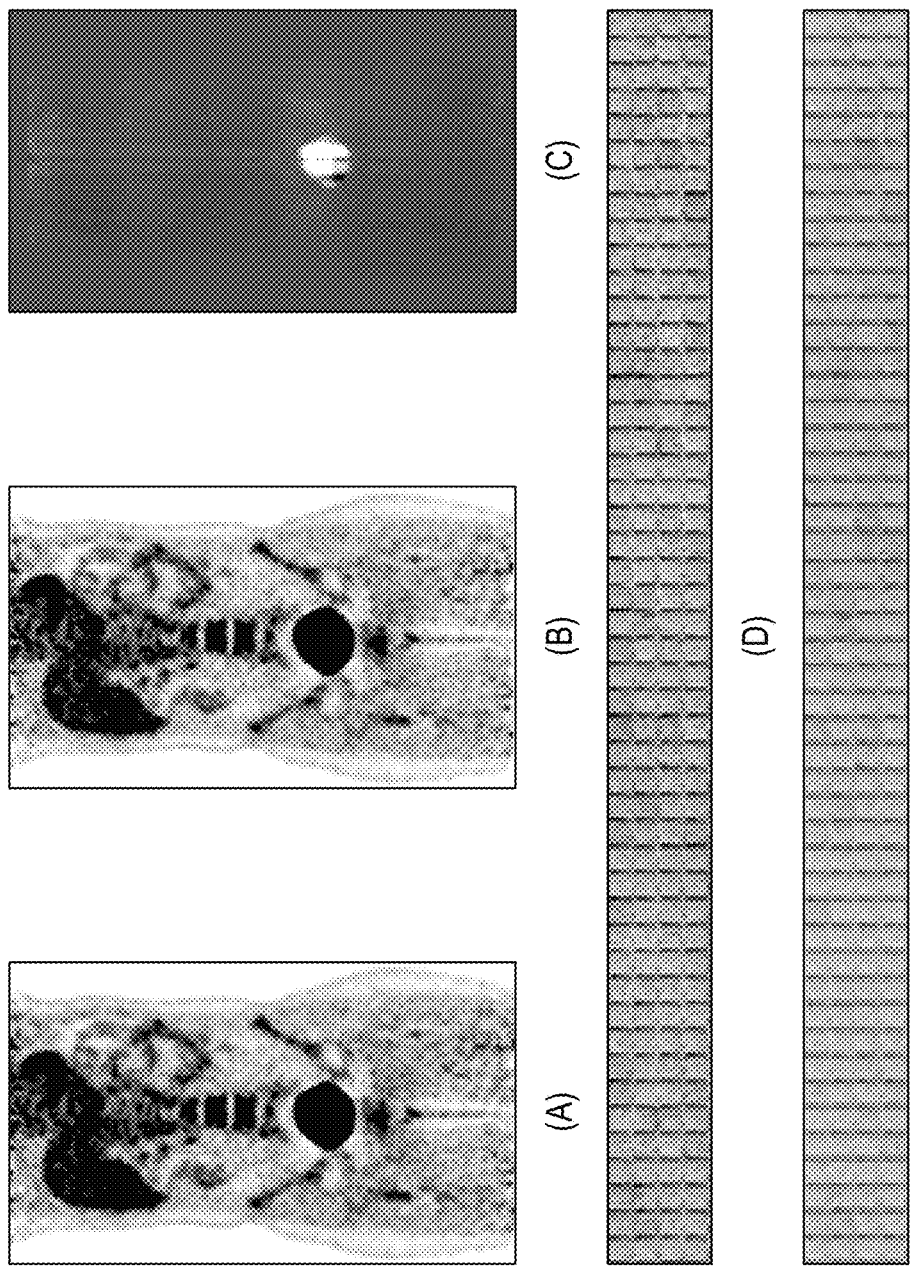
FIG. 3 shows the first patient data set. (A) shows ML-ACE activity reconstruction; (B) shows OS-EM activity reconstruction with the use of gold standard efficiencies; (C) this image reflects the difference between the images of (A) and (B); (D) shows ML-ACE crystal efficiency estimation; and (E) shows gold standard crystal efficiency estimation.

FIG. 3 presents the reconstruction of the first patient data set. There is no noticeable difference in activity reconstruction images. The different images showed deviations of up to about 2%. FIG. 3 (A) ML-ACE activity reconstruction. FIG. 3(B) show OS-EM activity reconstruction with use of gold standard efficiencies. FIG. 3(C) depicts an image that shows the difference between the image of 3(A) and 3(B). FIG. 3(D) depicts ML-ACE crystal efficiencies estimation and FIG. 3(E) shows gold standard crystal efficiencies.

A normalization pattern can be noticed in the image of FIG. 3(E). This is likely the result of different convergences in crystal efficiencies. A visual inspection of the crystal efficiencies in the FIGS. 3(D) and 3(E) reveal the same block patterns. For example, the same blocks showed slightly suppressed overall sensitivities. Nevertheless, the ML-ACE efficiencies map gives the impression of a less noisy estimate, which can be partly due to the use of the Gaussian model in the estimation of the gold standard.

Figure 4:
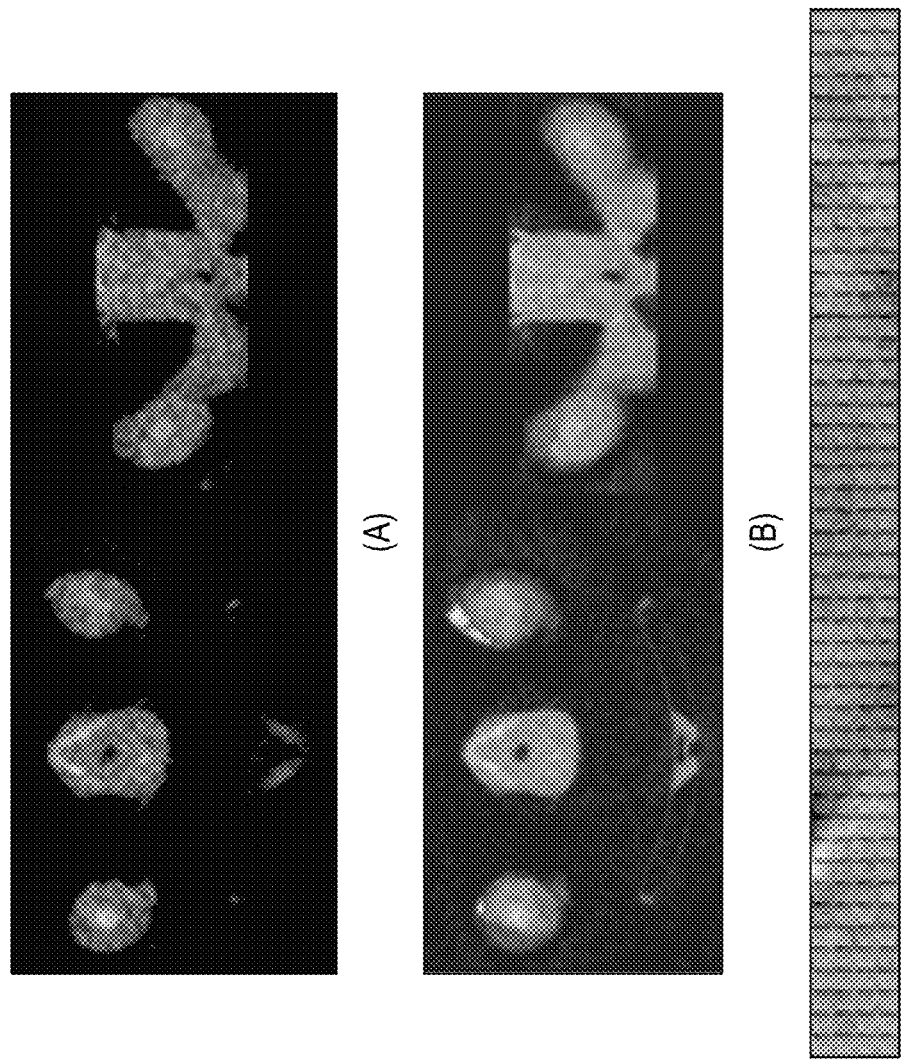
FIG. 4 shows the neck region data for the first patient data set 1. (A) shows a ML-AA reconstruction of attenuation map using gold standard normalization; (B) shows the image (A) fused with the CT attenuation map (color); (C) shows ML-ACE crystal efficiencies with the use of CT based attenuation map.

The FIG. 4 presents the crystal efficiencies estimations from data from the neck region. The artifact can be observed; it affects a few of the blocks. FIG. 4 (A) depicts ML-AA reconstruction of attenuation map using gold standard normalization. FIG. 4(B) shows image (a) fused with the CT attenuation map, while FIG. 4(C) shows ML-ACE crystal efficiencies with use of CT based attenuation map. Reconstruction of the attenuation map from emission data by TOF ML-AA algorithm described in V. Y. Panin, M. Aykac, and M. E. Casey, "Simultaneous reconstruction of emission activity and attenuation coefficient distribution from TOF data, acquired with external transmission source," Phys. Med. Biol., vol. 58, pp. 3649-3669, 2013, showed that the position of arms in the PET scan were different than that of the CT-based attenuation map. It is assumed that undetected motion resulted in the wrong attenuation information and eventually in artifacts in the efficiencies estimation.

Figure 5:
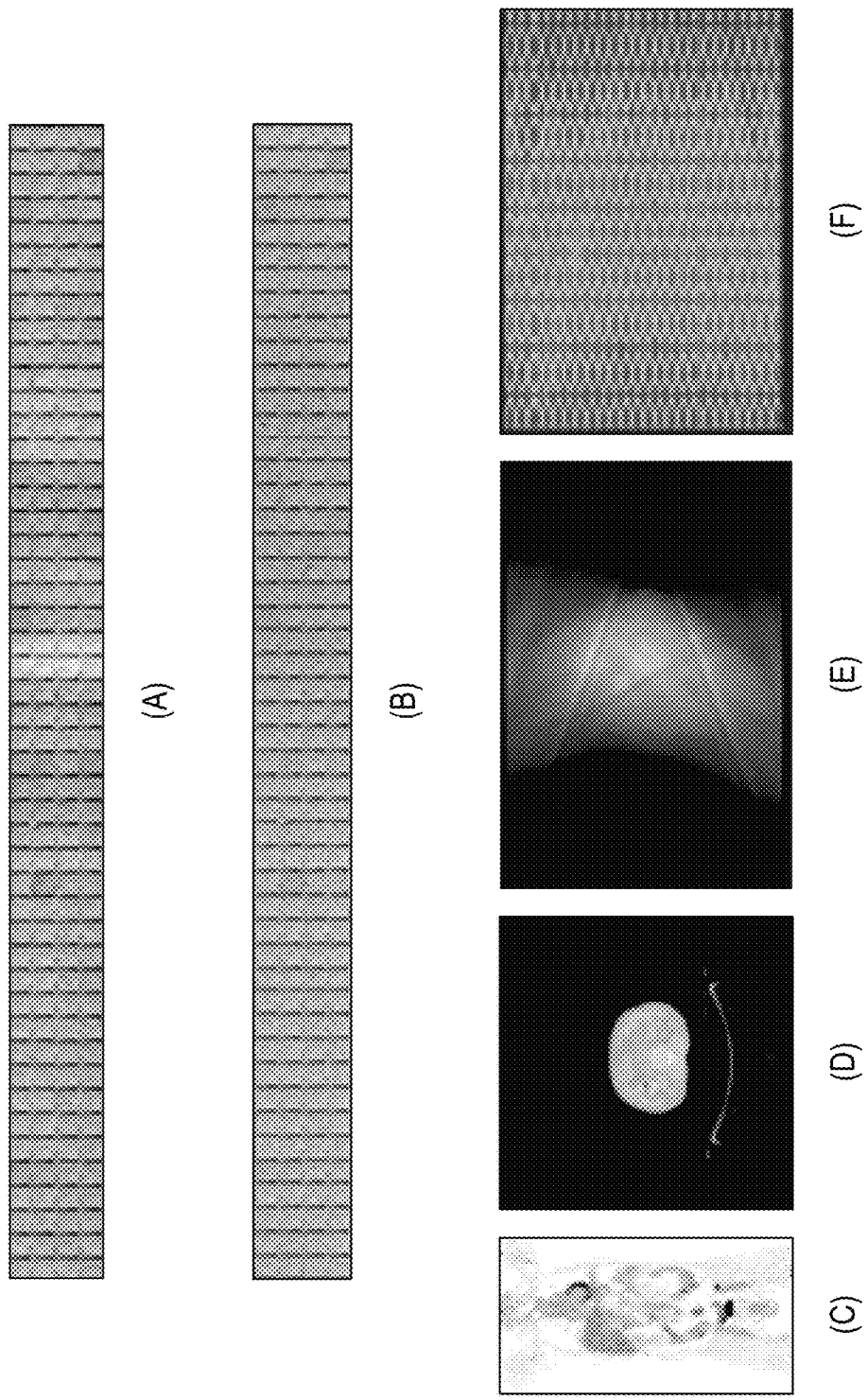
FIG. 5 presents the crystal efficiencies estimation from the second patient data set. (A) shows the ML-ACE crystal efficiency (B) shows gold standard crystal efficiency estimation (C) depicts ML-ACE activity reconstruction; (D) shows a one slice of attenuation map; (E) depicts the ACF's sinogram; and (F) shows a normalization array using crystal efficiencies of the FIG. 5(A)

FIG. 5 presents the crystal efficiencies estimation from the second patient data set. The ML-ACE and gold standard crystal efficiencies distributions coincided in uncommon block patterns. Nevertheless, there were several blocks with evaluated values in estimated efficiencies from patient data, according to the FIG. 5(A). The FIG. 5(A) depicts the ML-ACE crystal efficiencies. The FIG. 5(B) shows gold standard crystal efficiencies estimations. The FIG. 5(C) depicts ML-ACE activity reconstruction. FIG. 5(D) one slice of attenuation map. FIG. 5(E) depicts the ACF's sinogram, and the FIG. 5(F) shows a normalization array with crystal efficiencies of the FIG. 5(A).

Figure 6:
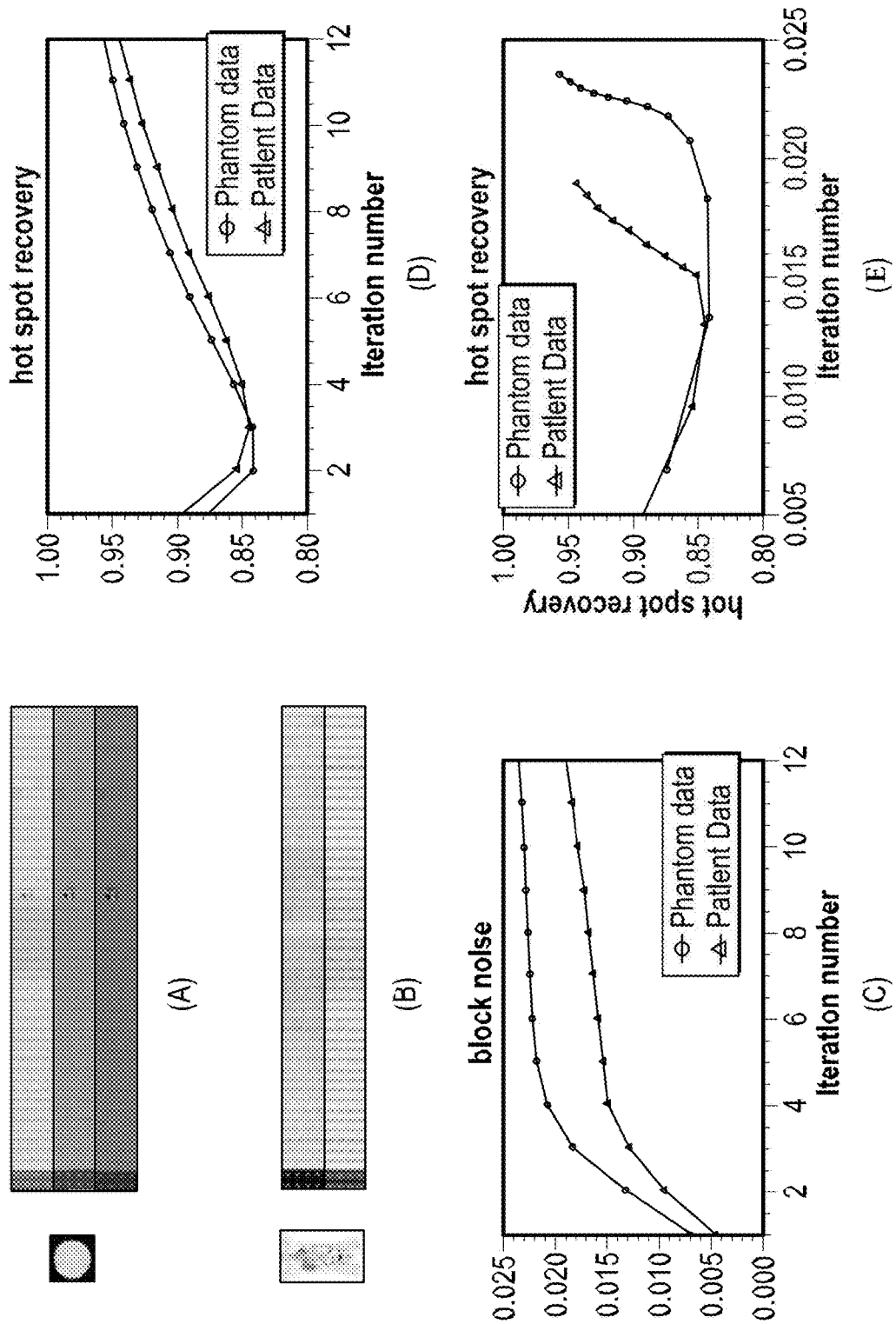
FIG. 6 shows hot spot recovery versus crystal efficiencies' estimation noise. (A) shows crystal efficiencies estimation from phantom data. The top image is the $1^{st}$ iteration, middle image is the $12^{th}$ iteration and bottom image is the $50^{th}$ iteration; (B) Crystal efficiencies estimation from patient data. The top image is the effective $1^{st}$ iteration; the bottom image is the effective $12^{th}$ iteration; (C) Noise versus iteration number; (D) Hot spot recovery versus iteration number; (E) hot spot recovery versus noise.

FIG. 6 shows hot spot recovery versus crystal efficiencies' estimation noise. FIG. 6(A) shows crystal efficiencies estimation from phantom data. The top image is the $1^{st}$ iteration, the middle image is the $12^{th}$ iteration and the bottom image is the $50^{th}$ iteration. FIG. 6(B) shows crystal efficiencies estimation from patient data. The top image is the effective $1^{st}$ iteration while the bottom image is the effective $12^{th}$ iteration. FIG. 6(C) shows noise versus iteration number. FIG. 6(D) shows hot spot recovery versus iteration number and the FIG. 6(E) hot spot recovery versus noise. FIG. 6(C)-6(E) show estimation from patient and phantom data. The hot spots in the FIG. 6(A) display elongated tails in the axial direction at earlier iterations due to the sinogram span's relatively large value of 11. The shape of the hot spots was restored at later iterations. FIG. 6(C) shows that the ML-ACE resulted in a less noisy estimation for a given iteration number. FIG. 6(D) shows that the ML-ACE results in slightly slower recovery of hot spots. Overall, recovery—noise trade-offs are better with ML-ACE, according to the FIG. 6(E).

With ML-AA and ML-ACF algorithms, attenuation estimation is of little interest. These methods can be currently considered as being complimentary to the gold standard CT or MR-based attenuation information due to significant noise build up in the estimation from emission data only. The goal behind these algorithms is to achieve activity estimation that is free of attenuation artifacts. Contrary to this, the primary goal of the ML-ACE is crystal efficiency estimation, which is itself a sub-product of activity reconstruction that is free of normalization artifacts. This example shows that the use of a crystal efficiencies constraint on a normalization array can result in reliable information about detector performance. Despite the fact that patient data consisted of a smaller number of trues, the ML-ACE resulted in better quality estimation of crystal efficiencies compared with the currently-used daily check estimation.

The method disclosed herein relies on the correctness of attenuation information. The crystal efficiencies were estimated well in the patient torso area. In the neck area estimation, an arm motion artifact extended over a few adjacent blocks. Potentially, such artifact patterns can be used in detection of motion. If motion is detected, then the ML-AA/ACF can be dispatched to complete CT-based attenuation information.

The method detailed herein aims to eliminate frequent daily check scans of known, specially designed objects. There are other less frequent calibration procedures, such as time alignment and detector setup. Time alignment can be performed based on patient data as well. The detector setup, which includes PMT gain adjustment, photo peak alignment, and crystal position map definition, can be potentially performed based on the LSO background radiation.

It is to be noted that all ranges detailed herein include the endpoints. Numerical values from different ranges are combinable.

The transition term comprising encompasses the transition terms "consisting of" and "consisting essentially of".

The term "and/or" includes both "and" as well as "or". For example, "A and/or B" is interpreted to be A, B, or A and B.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A method for calibrating a positron emission tomography detector of a radiation therapy device, the method comprising:
    applying, using a radiotherapy device, at least one defined radiation dose in a living sample body to induce a defined activity in the living sample body, the at least one defined radiation dose being applied by irradiating the living sample body with a treatment radiation beam of the radiotherapy device; where the positron emission tomography detector comprises at least one bin;
    measuring the activity generated by the at least one defined radiation dose in the at least one bin;
    taking projection data of the measured activity;
    calculating crystal efficiency from the projection data;
    re-estimating the measured activity of each bin based on the calculated crystal efficiency; and
    calibrating the bin based on the re-estimated measured activity, where the taking projection data of the measured activity and calculating crystal efficiency from the projection data comprises maximizing the Equations:

$$L(\varepsilon, f) = \sum_{jt} (y_{jt} \ln(\bar{y}_{jt}) - \bar{y}_{jt}) \quad (4)$$

$$\bar{y}_{jt} = a_j n_j^1(\varepsilon) \sum_k C_{jt,k} f_k - n_j^1(\varepsilon) S_{jt} + \bar{r}_{jt} = a_j n_j^1(\varepsilon) \bar{p}_{jt}(f) + n_j^1(\varepsilon) S_{jt} - \bar{r}_{jt} \quad (1)$$

and $$n_j^{-1}(\varepsilon) = \sum_{i,i'} \omega_{j,ii'} g_{ii'} \varepsilon_i \varepsilon_{i'}, \quad (2)$$

where ε is the crystal efficiency, g is the geometrical component of the normalization array, f is the activity image, a represents the attenuation, y represents the measured prompts, S represents the scatter estimation, r represents the smoothed randoms, C represents the system matrix, g represents the geometrical part of normalization, L represents the line of response, Equation (2) represents rebinning of a line or responses connecting two crystals i and i' into the projection bin of index j, where ω is the line of response contribution factor and where for the Equation (2), where Equation (2) represents the mashing and rebinning of the line of responses connecting two crystals i and i' into the projection bin of index j; where for the Equation (2):

$$\omega_{j,ii'} = \begin{cases} 1/2, & \text{if } ii' \text{ contribute to sinogram bin } j \\ 0, & \text{otherwise} \end{cases} \quad (3)$$

2. The method of claim 1, where the bin is recalibrated if it deviates from a standard.

3. The method of claim 2, where the detector comprises a plurality of bins.

4. The method of claim 1, where taking projection data of the measured activity comprises reconstructing the measured activity at a given crystal efficiency.

5. The method of claim 1, where calculating the crystal efficiency is conducted by measuring time of flight data.

6. The method of claim 5, where calculating the crystal efficiency comprises modifying a maximum likelihood algorithm with the measured time of flight data.

7. The method of claim 1, where the re-estimating efficiencies is conducted using an iterative algorithm, presented by Equation (5) below:

$$\varepsilon_i^{(N+1)} = \frac{-B_i + \sqrt{B_i^2 + 4A_i C_i}}{2A_i} \quad (5)$$

$$A_i = \sum_{jt} \sum_{i'} \omega_{j,ii'} g_{ii'} (a_j \bar{p}_{jt}(f) + S_{jt}),$$

$$B_i = \sum_{jt} \sum_{i'} \omega_{j,ii'} (a_j \bar{p}_{jt}(f) + S_{jt}) \varepsilon_{i'}^{(N)} - A_i \varepsilon_i^{(N)}$$

$$C_i = \varepsilon_i^{(N)} \sum_{jt} \frac{y_{jt}}{\bar{y}_{jt}^{(N)}(f, \varepsilon^{(N)})} \sum_{i'} \omega_{j,ii'} (a_j \bar{p}_{jt}(f) + S_{jt}) \varepsilon_{i'}^{(N)},$$

where N is the iteration number for updating crystal efficiency.

8. The method of claim 7, where N can be any integer from 1 to 50.

9. The method of claim 1, where the bin or the detector is replaced if the re-estimated measured activity falls outside a desired range.

10. The method of claim 1, where the bin is shut-off if the re-estimated measured activity falls outside a desired range.

11. A positron emission tomography calibration system comprising:
- a positron emission tomography scanner having a ring detector that comprises at least one bin for receiving radiation;
- a patient that is placed at approximately the center of the ring detector where the patient is irradiated with at least one dose of a treatment radiation beam;
- a crystal efficiency calibration system that performs the following:
- measures activity generated by the at least one defined radiation dose in the at least one bin;
- takes projection data of the measured activity;
- calculates crystal efficiency from the projection data;
- re-estimates the measured activity of each bin based on the calculated crystal efficiency; and
- calibrates the detector based on the re-estimated measured activity,
- where the taking projection data of the measured activity and calculating crystal efficiency from the projection data comprises maximizing the Equations:

$$L(\varepsilon, f) = \sum_{jt} (y_{jt} \ln(\bar{y}_{jt}) - \bar{y}_{jt}) \quad (4)$$

$$\bar{y}_{jt} = a_j n_j^{-1}(\varepsilon) \sum_k C_{jt,k} f_k - n_j^{-1}(\varepsilon) S_{jt} + \bar{r}_{jt} = \quad (1)$$

$$a_j n_j^{-1}(\varepsilon) \bar{p}_{jt}(f) + n_j^{-1}(\varepsilon) S_{jt} - \bar{r}_{jt}$$

and $$n_j^{-1}(\varepsilon) = \sum_{i,i'} \omega_{j,ii'} g_{ii'} \varepsilon_i \varepsilon_{i'}, \quad (2)$$

where ε is the crystal efficiency, g is the geometrical component of the normalization array, f is the activity image, a represents the attenuation, y represents the measured prompts, S represents the scatter estimation, r represents the smoothed randoms, C represents the system matrix, g represents the geometrical part of normalization, L represents the line of response, Equation (2) represents rebinning of a line or responses connecting two crystals i and i' into the projection bin of index j, where ω is the line of response contribution factor and where for the Equation (2), where Equation (2) represents the mashing and rebinning of the line of responses connecting two crystals i and i' into the projection bin of index j; where for the Equation (2):

$$\omega_{j,ii'} = \begin{cases} 1/2, & \text{if } ii' \text{ contribute to sinogram bin } j \\ 0, & \text{otherwise} \end{cases} \quad (3)$$

12. The system of claim 11, where the detector comprises a plurality of bins.

13. The system of claim 11, where taking projection data of the measured activity comprises reconstructing the measured activity at a given crystal efficiency.

14. The system of claim 11, where calculating the crystal efficiency is conducted by measuring time of flight data.

15. The system of claim 11, where the re-estimating efficiencies is conducted using an iterative algorithm, presented by Equation (5) below:

$$\varepsilon_i^{(N+1)} = \frac{-B_i + \sqrt{B_i^2 + 4A_i C_i}}{2A_i} \quad (5)$$

$$A_i = \sum_{jt} \sum_{i'} \omega_{j,ii'} g_{ii'}(a_j \bar{p}_{jt}(f) + S_{jt}),$$

$$B_i = \sum_{jt} \sum_{i'} \omega_{j,ii'}(a_j \bar{p}_{jt}(f) + S_{jt})\varepsilon_{i'}^{(N)} - A_i \varepsilon_i^{(N)}$$

$$C_i = \varepsilon_i^{(N)} \sum_{jt} \frac{y_{jt}}{\bar{y}_{jt}^{(N)}(f, \varepsilon^{(N)})} \sum_{i'} \omega_{j,ii'}(a_j \bar{p}_{jt}(f) + S_{jt})\varepsilon_{i'}^{(N)},$$

where N is the iteration number for updating crystal efficiency.

16. The system of claim 11, where N can be any integer from 1 to 50.

17. The system of claim 11, where the bin or the detector is replaced if the re-estimated measured activity falls outside a desired range.

18. The system of claim 11, where the bin is shut-off if the re-estimated measured activity falls outside a desired range.

\* \* \* \* \*